(12) United States Patent
Park

(10) Patent No.: US 9,480,584 B2
(45) Date of Patent: Nov. 1, 2016

(54) MEDICAL DEVICE

(71) Applicant: RBKPARK LLC, St. Charles, IL (US)

(72) Inventor: Richard Park, St. Charles, IL (US)

(73) Assignee: RBKPARK LLC, St. Charles, IL (US)

( * ) Notice: Subject to any disclaimer, the term of this patent is extended or adjusted under 35 U.S.C. 154(b) by 79 days.

(21) Appl. No.: 14/581,584

(22) Filed: Dec. 23, 2014

(65) Prior Publication Data

US 2016/0030208 A1    Feb. 4, 2016

Related U.S. Application Data

(63) Continuation of application No. 12/782,410, filed on May 18, 2010, now Pat. No. 8,920,486.

(51) Int. Cl.

| | |
|---|---|
| *A61F 2/06* | (2013.01) |
| *A61F 2/844* | (2013.01) |
| *A61B 5/00* | (2006.01) |
| *A61B 5/107* | (2006.01) |
| *A61B 6/12* | (2006.01) |
| *A61B 6/00* | (2006.01) |
| *A61F 2/95* | (2013.01) |

(52) U.S. Cl.
CPC ............. *A61F 2/844* (2013.01); *A61B 5/0059* (2013.01); *A61B 5/1076* (2013.01); *A61B 6/12* (2013.01); *A61B 6/504* (2013.01); *A61F 2/95* (2013.01); *A61B 2090/3966* (2016.02); *A61F 2002/065* (2013.01); *A61F 2230/0071* (2013.01); *A61F 2250/0096* (2013.01); *A61F 2250/0098* (2013.01)

(58) Field of Classification Search
CPC ............. A61F 2/82; A61F 2/07; A61F 2/90; A61F 2/91; A61F 2/915; A61F 2250/0098; A61L 31/18; A61L 31/06

See application file for complete search history.

(56) References Cited

U.S. PATENT DOCUMENTS

| | | |
|---|---|---|
| 5,353,807 A | 10/1994 | DeMarco |
| 5,725,572 A | 3/1998 | Lam et al. |
| 5,733,302 A | 3/1998 | Myler et al. |
| 5,746,766 A | 5/1998 | Edoga |
| 6,171,329 B1 | 1/2001 | Shaw et al. |
| 6,203,568 B1 | 3/2001 | Lombardi et al. |
| 6,231,598 B1 | 5/2001 | Berry et al. |
| 6,251,135 B1 | 6/2001 | Stinson et al. |

(Continued)

OTHER PUBLICATIONS

Article from eMedicine, Percutaneous Transluminal Coronary Angioplasty, http://www.emedicine.com/med/topic3199.htm, Aug. 22, 2005.

(Continued)

*Primary Examiner* — Thomas J Sweet
*Assistant Examiner* — Tiffany Shipmon
(74) *Attorney, Agent, or Firm* — Banner & Witcoff, Ltd.

(57) ABSTRACT

Novel devices and methods for implanting medical stents are provided. A novel apparatus, which may be in a first compressed position, may be inserted into the artery, such as by being positioned over a catheter. The apparatus may be expanded to a second position. In one embodiment, the apparatus is configured to expand away in two substantially opposing directions along a second axis away from the longitudinal axis. The second axis may be perpendicular to the longitudinal axis. The apparatus may include markers that are detectable to determine the orientation of the catheter or the apparatus and/or assist in the determination of the type or size of stent to utilize.

17 Claims, 17 Drawing Sheets

(56) References Cited

U.S. PATENT DOCUMENTS

| | | |
|---|---|---|
| 6,285,898 B1 | 9/2001 | Ben-Haim |
| 6,334,871 B1 | 1/2002 | Dor et al. |
| 6,363,940 B1 | 4/2002 | Krag |
| 6,464,720 B2 | 10/2002 | Boatman et al. |
| 6,582,394 B1 | 6/2003 | Reiss et al. |
| 6,599,316 B2 | 7/2003 | Vardi et al. |
| 6,749,628 B1 | 6/2004 | Callol et al. |
| 6,896,699 B2 | 5/2005 | Wilson et al. |
| 8,535,370 B1 | 9/2013 | Eckert et al. |
| 2001/0012961 A1 | 8/2001 | Deem et al. |
| 2003/0028233 A1 | 2/2003 | Vardi et al. |
| 2003/0199967 A1 | 10/2003 | Hartley et al. |
| 2005/0013686 A1 | 1/2005 | Schiavo |
| 2005/0060028 A1 | 3/2005 | Horres et al. |
| 2005/0131518 A1 | 6/2005 | Hartley et al. |
| 2005/0203568 A1 | 9/2005 | Burg et al. |
| 2006/0030926 A1 | 2/2006 | Berra |
| 2006/0106455 A1 | 5/2006 | Furst et al. |
| 2006/0155357 A1 | 7/2006 | Melsheimer |
| 2007/0142900 A1 | 6/2007 | Balaji |

OTHER PUBLICATIONS

Article from Journal of the American College of Cardiology, Aug. 16, 2005, vol. 46, No. 4, Revascularization in Severe Left Ventricular Dysfunction: The Role of Viability Testing, Chareonthaitawee, et al., p. 567.

Article from Journal of the American College of Cardiology, Aug. 16, 2005, vol. 46, No. 4, Five-Year Outcomes After Coronary Stenting Versus Bypass Surgery for the Treatment of Multivessel Disease: The Final Analysis of the Arterial Revascularization Therapies Study (AETS) Randomized Trial, Serruys, et al., p. 575.

Article from Journal of the American College of Cardiology, Aug. 16, 2005, vol. 46, No. 4, Five-Year Follow-Up of the Argentine Randomized Trial of Coronary Angioplasty With Stenting Versus Coronary Bypass Surgery in Patients With Multiple Vessel Disease (ERACI II), Rodriquez, et al., p. 582.

Article from Journal of the American College of Cardiology, Aug. 16, 2005, vol. 46, No. 4, Stenting or Surgery: An Opportunity to Do It Right, Robert M. Califf, M.D., FACC, p. 589.

Article from Journal of the American College of Cardiology, Aug. 16, 2005, vol. 46, No. 4, The FRONTIER Stent Registry: Safety and Feasibility of a Novel Dedicated Stent for the Treatment of Bifurcation Coronary Artery Lesions, Lefevre, et al., p. 592.

Article from Journal of the American College of Cardiology, Aug. 16, 2005, vol. 46, No. 4, Bifurcation Coronary Lesions Treated With the "Crush" Technique, An Intravascular Ultrasound Analysis, Costa, et al., p. 599.

Article from Journal of the American College of Cardiology, Aug. 16, 2005, vol. 46, No. 4, Nine-Month Outcome of Patients Treated by Percutaneous Coronary Interventions for Bifurcation Lesions in the Recent Era: A report From the Prevention of Restenosis With Tranilast and its Outcomes (PRESTO) Trial; Garot, et al., p. 606.

Article from Journal of the American College of Cardiology, Aug. 16, 2005, vol. 46, No. 4, Clinical and Angiographic Outcome After Implantation of Drug-Eluting Stents in Bifurcation Lesions With the Crush Stent Technique, Importance of Final Kissing Balloon Post-Dilation, Ge, et al., p. 613.

Article from Journal of the American College of Cardiology, Aug. 16, 2005, vol. 46, No. 4, Bifurcation Intervention: Is it Crush Time Yet? Williams, et al., p. 621.

Article from Journal of the American College of Cardiology, Aug. 16, 2005, vol. 46, No. 4, Relationship Between Operator Volume and Adverse Outcome in Contemporary Percutaneous Coronary Intervention Practice: An Analysis of a Quality-Controlled Multicenter Percutaneous Coronary Intervention Clinical Database, Moscucci, et al., p. 625.

Article from Journal of the American College of Cardiology, Aug. 16, 2005, vol. 46, No. 4, Physiologic Assessment of Jailed Side Branch Lesions Using Fractional Flow Reserve, Koo, et al., p. 633.

Article from Journal of the American College of Cardiology, Aug. 16, 2005, vol. 46, No. 4, Matching the Evaluation of the Clinical Efficacy of Clopidogrel to Platelet Function Tests Relevant to the Biological Properties of the Drug, Labarthe, et al., p. 638.

Article from Journal of the American College of Cardiology, Aug. 16, 2005, vol. 46, No. 4, Clopidogrel: Linking Evaluation of Platelet Response Variability to Mechanism of Action, Frelinger, et al., p. 646.

Article from Journal of the American College of Cardiology, Aug. 16, 2005, vol. 46, No. 4, Endothelial Vasomotor Dysfunction in the Brachial Artery Is Associated With Late In-Stent Coronary Restenosis, Kitta, et al., p. 648.

Article from Journal of the American College of Cardiology, Aug. 16, 2005, vol. 46, No. 4, Impaired Endothelial Function in Coronary Heart Disease Patients With Depressive Symptomatology, Sherwood, et al., p. 656.

Article from Journal of the American College of Cardiology, Aug. 16, 2005, vol. 46, No. 4,The Economic Effect of a Tertiary Hospital-Based Heart Failure Program, Gregory, et al., p. 660.

Article from Journal of the American College of Cardiology, Aug. 16, 2005, vol. 46, No. 4,Electrogram Characteristics in Postinfarction Ventricular Tachycardia: Effect of Infarct Age, Bogun, et al., p. 667.

Article from Journal of the American College of Cardiology, Aug. 16, 2005, vol. 46, No. 4, "The Older the Broader": Electrogram Characteristics Help Identify the Critical Isthmus During Catheter Ablation of Postinfarct Ventricular Tachycardia, Klein, et al., p. 675.

Article from Journal of the American College of Cardiology, Aug. 16, 2005, vol. 46, No. 4, The Combined Use of Ibutilide as an Active Control With Intensive Electrocardiographic Sampling and Signal Averaging as a Sensitive Method to Assess the Effects of Tadalafil on the Human QT Interval, Beasley, Jr. et al., p. 678.

Article from Journal of the American College of Cardiology, Aug. 16, 2005, vol. 46, No. 4, Making a Silk Purse Out of a Sow's Ear, Kowey, et al., p. 688.

Article from Journal of the American College of Cardiology, Aug. 16, 2005, vol. 46, No. 4, Prevalence and Clinical Significance of Left Atrial Remodeling in Competitive Athletes, Pelliccia, et al., p. 690.

Article from Journal of the American College of Cardiology, Aug. 16, 2005, vol. 46, No. 4, Effects of Long-Term Bosentan in Children With Pulmonary Arterial Hypertension, Rosenzweig, et al., p. 697.

Article from Journal of the American College of Cardiology, Aug. 16, 2005, vol. 46, No. 4, Improving the Outcome of Childhood Pulmonary Arterial Hypertension: The Effect of Bosentan in the Setting of a Dedicated Pulmonary Hypertension Clinic, Ian Adatia, MBCHB, p. 705.

Article from Journal of the American College of Cardiology, Aug. 16, 2005, vol. 46, No. 4, Plasma Tissue Factor Plus Activated Peripheral Mononuclear Cells Activate Factors VII and X in the Cardiac Surgical Wounds, Hattori, et al., p. 707.

Article from Journal of the American College of Cardiology, Aug. 16, 2005, vol. 46, No. 4, Thickening of the Infarcted Wall by Collagen Injections Improves Left Ventricular Function in Rats: A Novel Approach to Preserve Cardiac Function After Myocardial Infarction, Dai, et al., p. 714.

Article from Journal of the American College of Cardiology, Aug. 16, 2005, vol. 46, No. 4, Functional and Morphologic Imaging of Coronary Atherosclerosis in Living Mice Using High-Resolution Color Doppler Echocardiography and Ultrasound Biomiropscopy, Wikström, et al., p. 720.

Article from Journal of the American College of Cardiology, Aug. 16, 2005, vol. 46, No. 4, The Department of Cardiac/Vascular Medicine and Surgery, Anthony N. DeMaria, MD, MACC, p. 728.

Article from Journal of the American College of Cardiology, Aug. 16, 2005, vol. 46, No. 4, Research Correspondence, Risk Stratification of Patients With Classic Angina Pectoris and No History of Coronary Artery Disease by Dobutamine Stress Echocardiography, Biagini, et al., p. 730.

International Search Report in related International Patent Application No. PCT/US06/34411, pp. 1-9, Sep. 25, 2007.

Schneller et al., "Contrast Media as Carriers for Local Drug Delivery Successful Inhibition of ; Neointimal Proliferation in the Porcine Coronary Stent Model", European Heart Journal (2003) 24, 1462-1467: ; p. 1466, para. 2 and 5-6.

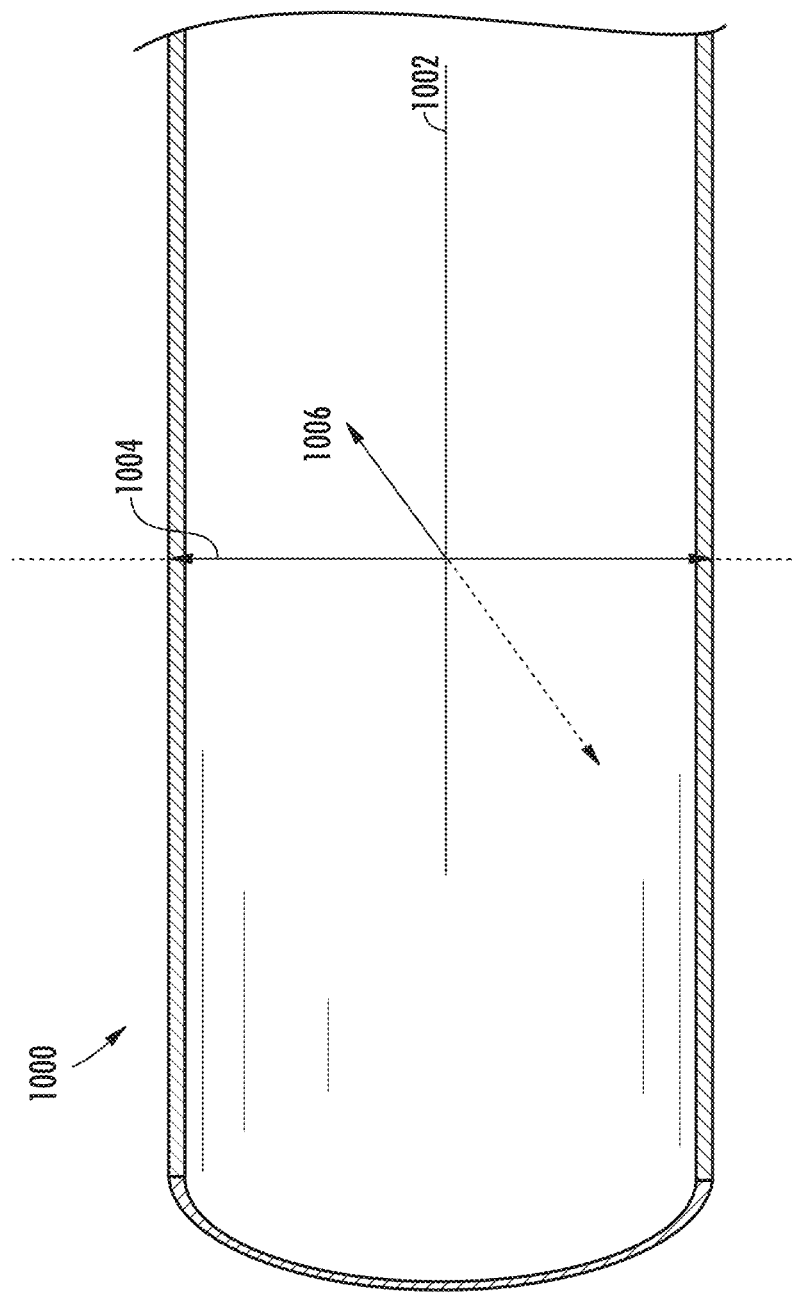

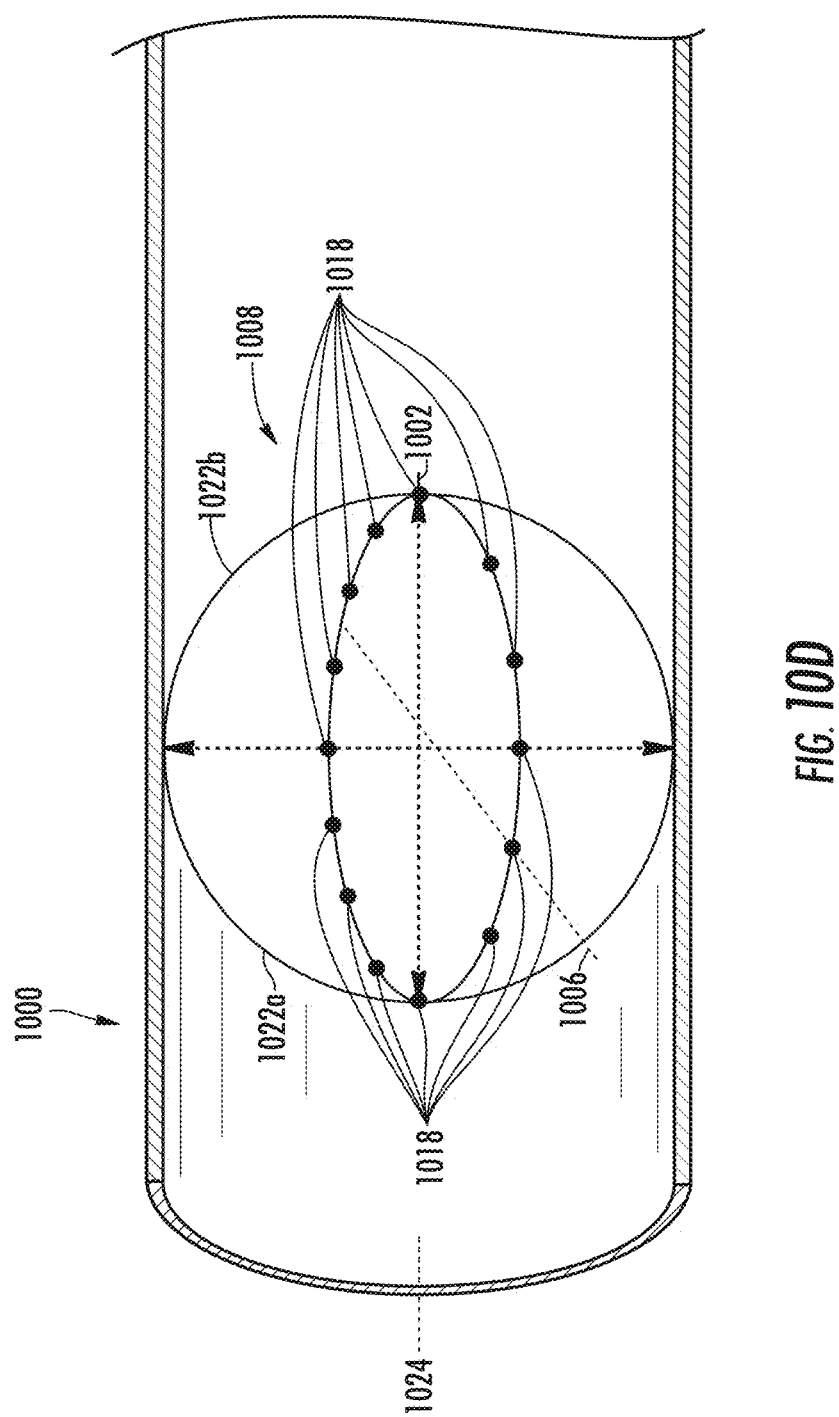

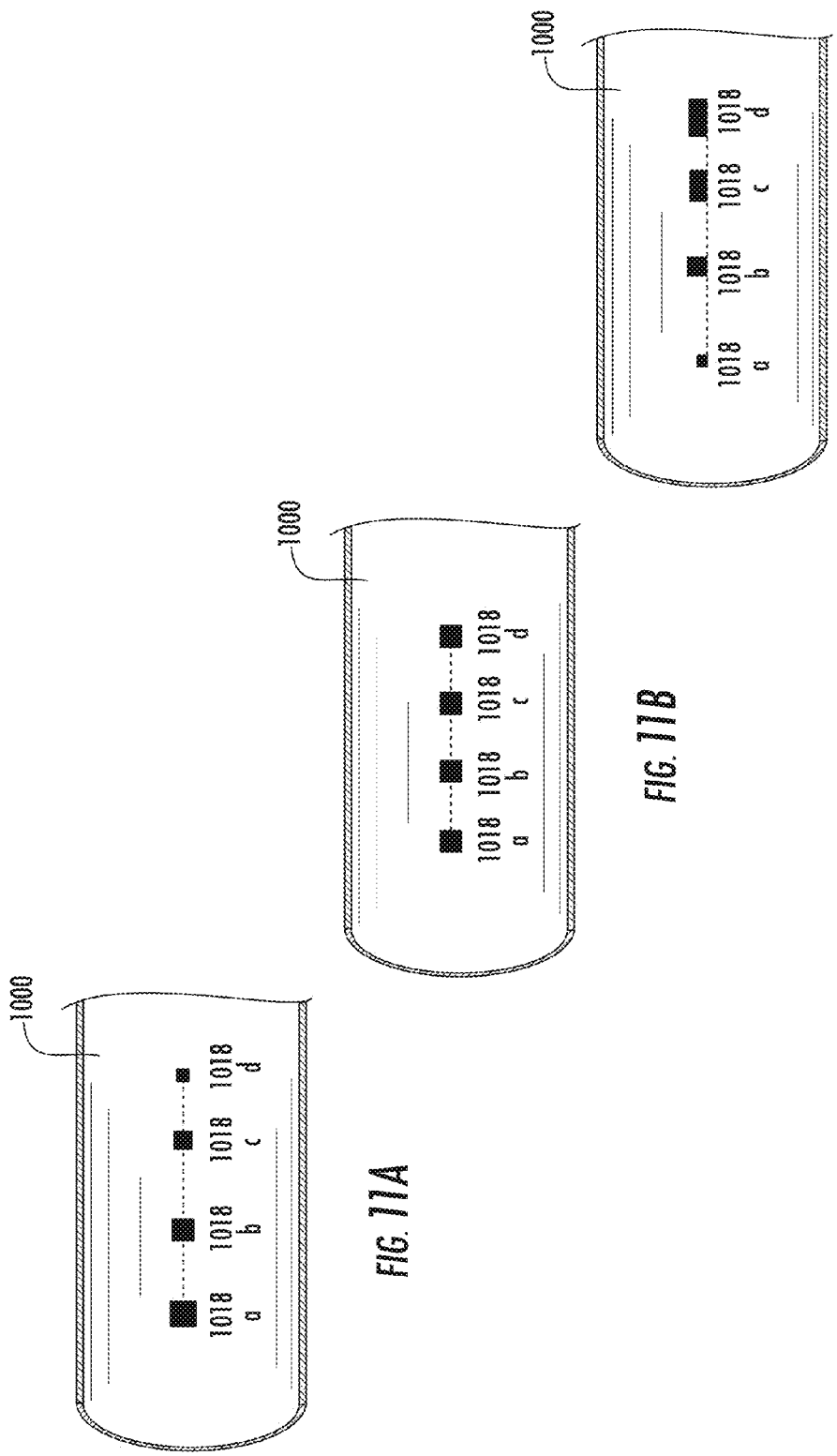

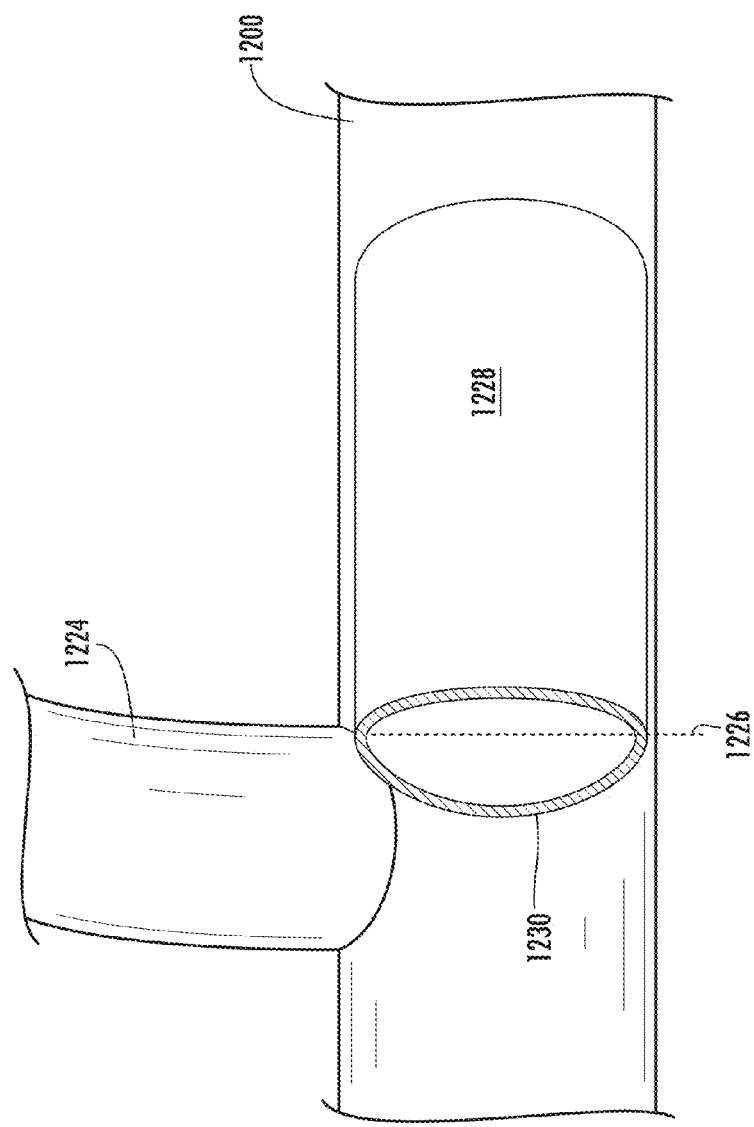

MEDICAL DEVICE

CROSS-REFERENCE TO RELATED APPLICATIONS

This application is a continuation of U.S. patent application Ser. No. 12/782,410, entitled "MEDICAL DEVICE," filed May 18, 2010, which is expressly incorporated herein by reference in its entirety for any and all non-limiting purposes.

BACKGROUND

As is known, the human heart circulates blood throughout the body. Depending on the individual, the heart beats between 80,000 and 140,000 times per day. During normal function of the heart, the left and right atria and the left and right ventricles contract, causing blood to flow. The blood flows from the heart, passes through a set of blood vessels known as arteries that feed the organs and tissue in the body and then returns to the heart through a set of blood vessels known as veins. This circulation provides nutrients and oxygen to the body so that it can continue to function.

As the heart is basically a continuously functioning muscle, it also needs a steady supply of nutrients in order to function. For example, a coronary artery supplies blood (and the associated oxygen and nutrients) to the cardiac muscle. In order for the heart to continue to function, it is crucial that this artery continue to function properly.

Unfortunately, the coronary artery can become partially or completely blocked. One cause is left main coronary artery disease ("LMCD"). LMCD may be caused, for example, by the accumulation of fatty tissue on the wall of the left main artery. LMCD is generally defined as a greater than 50% reduction in the left main, which results in insufficient blood flow to the heart tissue and eventually causes damage to the heart tissue.

While partial blockage can result in permanent damage to the heart muscle, sudden complete blockage of the left main will result in the death of the individual. Therefore, maintaining blood flow through the left main is crucial to an individual's ability to exist. Any symptomatic blockage must be immediately treated.

Two methods of treatment of a partially or completely blocked left main are 1) percutaneous transluminal coronary angioplasty ("PTCA"), also referred to as percutaneous coronary intervention ("PCI"), and commonly referred to as balloon angioplasty or angioplasty, and 2) coronary artery bypass graft ("CABG"), commonly referred to as bypass surgery. Due to a number of factors, the most common procedure to treat LMCD has been bypass surgery.

In essence, bypass surgery uses section of veins or arteries sections from other parts of the body to connect the aorta to a point downstream of the blockage. This allows blood to flow around the blockage point through a separate passageway. Depending on the severity and location of the blockage, as many as four to five grafts are necessary.

One downside to bypass surgery is that it takes a substantial time to perform. For a patient with a totally occlusion or a severely blocked left main, the time it takes to perform bypass surgery may be too long. Therefore, in emergencies, balloon angioplasty has been performed on patients suffering from sudden LMCD.

Another problem is that bypass surgery is only effective for about 8-10 years, at which point a patient generally requires additional treatment that is generally less effective. Given the potential long-term health problems, it is desirable to delay bypass surgery if possible.

Furthermore, certain patients' medical conditions are incompatible with the rigors of bypass surgery. For example, some patients have severe co-morbid conditions precluding open-heart surgery, such as malignancy with limited life-expectancy, no longer are a candidate for bypass surgery. Thus, while bypass surgery is a useful medical procedure that has saved many lives, it is best saved for situations where less complex procedures cannot be used effectively.

In addition, some interventional cardiac catheterization labs are not backed up by surgical programs. This is problematic in situations where the LMCD must be treated immediately (e.g. iatrogenic dissection of the left main).

Compared to bypass surgery, angioplasty can be done relatively quickly and is generally less traumatic to the patient. Basically, during angioplasty a wire is inserted into the artery. A flexible catheter is then guided along the wire. A balloon attached to the catheter is positioned in the left main at the point of blockage and the balloon is inflated to open the artery. To keep the artery open, a stent may be placed in the left main. One common method of delivering the stent is to wrap it around the balloon. Thus, the inflation of the balloon causes the stent to expand into position. The stent acts as a scaffolding to support the wall of the artery and, when coated with anti-restenotic agents, can be an alternative means of treating certain types of LMCD.

Sometimes blockage of the body's passageways occur at a junction. For example, blockage often occurs at the junction of the left main and the left anterior descending artery and the left circumflex artery. In such a situation, the medical practitioner must ensure that insertion of a stent or other medical device does not substantially occlude the junction. Practitioners often image the affected area (such as with an angiogram) to determine the proper placement of a stent or other implantable devices. Unfortunately, failure to precisely determine the proper orientation of the artery and/or the stent may result in placing the stent in a position that occludes the junction. For example, an image from a first perspective may prompt a practitioner to believe that a stent is properly aligned, however, a perspective shift may reveal that the stent is not aligned. Further, markers on the stent, indicate the orientation of the stent in relation to that perspective, not the orientation with respect to a second perspective, or the orientation of the stent with respect to the passageway.

This further complicated by the fact that secondary branches and angles between the different branches are varied from person to person as well as from junction to junction, making it difficult to accurately determine the proper sized stent. In fact, using a stent that is sized too small may cause the stent to angle within the vessel in a manner that blocks normal flow. Unfortunately, this problem may not be discovered using existing technologies. Another major limitation is that much higher operator skill is required to position such a stent quickly, thus making it more likely that such a stent will be improperly installed. Thus, methods and systems that allow more accurate selection and placement of stents are desirable. Further, other medical fields would greatly benefit from improved stents and methods for implanting stents.

BRIEF SUMMARY OF THE INVENTION

Aspects of the invention relate to medical stents and methods for implanting medical stents. One aspect relates to novel methods for more accurately inserting a stent in a passageway, such as an artery. In one embodiment, methods correct parallax, which under certain conditions, result in the misplacement of a stent within a junction. Certain methods may be implemented upon detecting a complication within a first passageway. In one embodiment, an angiogram is taken from a first perspective that may reveal at least a portion of the complication, such as an aneurism within the artery. A novel apparatus, which may be in a first compressed position, may be inserted into the artery. The novel apparatus may be positioned over a catheter. In one embodiment, the catheter may be a pigtail catheter.

Upon being placed within the lumen of the artery, the length of the apparatus may travel substantially along the longitudinal axis of the artery. The apparatus may be expanded to a second position. In one embodiment, the apparatus is configured to expand away in two substantially opposing directions along a second axis away from the longitudinal axis. The second axis may be perpendicular to the longitudinal axis. In one embodiment, the expansion of the apparatus may have a known predetermined expansion. The selection of such an apparatus may consider, among other factors, the type of passageway it will be expanded within and/or unique properties of the passageway within the specific living being. In other embodiments, the apparatus may expand until met with a predetermined force, such as meeting the inner perimeter of the artery.

Once expanded, the apparatus may comprise one or more markers positioned along at least a portion of the apparatus' length. In other embodiments, markers may be positioned along any major or minor axis, including but not limited to the width and/or depth of the expansion. Markers may be placed on an outer perimeter of the apparatus, and thus measure the diameter of the lumen of an artery. The apparatus may also have markers that are detectable when in the first unexpanded configuration. One or more groups of markers may be separated by a predetermined distance and a plurality of markers separated by a predetermined distance along the second axis.

In certain methods, a second image may be captured following the expansion of the apparatus to the second position. In one embodiment, one group of markers are detectable when using a first imaging technique and a second group of markers are detectable using a second imaging technique. In certain implementations, the orientation of the catheter or the apparatus may be determined based upon the second captured image. In further embodiments, imaging capturing equipment may be used to capture an image from a second perspective. In still further embodiments, the shape and/or the size of a stent may be determined based upon the positions of at least a portion of markers of the apparatus.

Aspects of the invention relate to novel apparatuses that may be positioned within a passageway, such as an artery, to overcome prior deficiencies in the art. In one embodiment, the novel apparatuses may be implemented in accordance with one or more methods described above. In one embodiment, the apparatus may be configured to be positioned around a catheter and inserted a passageway, such as an artery. In one embodiment, the catheter is a pig-tail catheter configured to dispense a contrast dye. The apparatus may be expanded from a first configuration to a second configuration. In one embodiment, the apparatus may be configured to have a known predetermined expansion. The selection of such an apparatus may consider, among other factors, the type of passageway it will be expanded within and/or unique properties of the passageway within the specific living being. In other methods, the apparatus may expand until met against a specific force, such as expanding until pressed against the inner perimeter of an artery.

The apparatus may expand along two substantially opposing directions along a second axis. The second axis may be the width or the depth in certain implementations. In one embodiment, the second axis will expand across the diameter of a passageway if its substantially cylindrical. Upon expansion to the second configuration, markers along at least a portion of the apparatus' length may be separated by a predetermined distance. Markers may also be positioned along the second axis or other locations. One group of markers may be detected by a first imaging technique while a second group of markers are configured to be detected by a second imaging technique. Furthermore, the length of the apparatus may increase as it expands from the first configuration to the second configuration.

The detection of one or more markers may allow the determination of the orientation of the catheter or the apparatus. Determination of one or more certain markers may further assist in determining another perspective, that when compared to the first perspective, reduces parallax effects. In certain embodiments, the detection of markers may indicate the proper size and/or type of stent that may be best suited. In other embodiments, markers may assist in determining the size of a junction between two or more branches, and/or the diameter of a second passageway while not required to be positioned within the second passageway. In one embodiment, a stent may be expanded so as to support a wall of the left main coronary artery while allowing blood to flow through the side aperture into one of the secondary branches with less likelihood that the placement of the stent will occlude the junction. In certain embodiment, the stent (including the extension) may be coated with a pharmaceutical agent.

BRIEF DESCRIPTION OF THE DRAWINGS

The present invention is illustrated by way of example and not limited in the accompanying figures in which like reference numerals indicate similar elements and in which:

FIGS. 10A-10E illustrates the placement of an exemplary apparatus into a passageway in accordance with one embodiment of the invention. Specifically, FIG. 10A shows the exemplary passageway prior to the insertion of the apparatus, FIG. 10B shows the apparatus being positioned in the passageway; FIG. 10C shows the exemplary apparatus following expansion within the passageway; and FIG. 10D shows another exemplary apparatus following expansion within the passageway. FIG. 10E shows the exemplary apparatus of FIG. 10D, however, from a different view.

FIGS. 11A-11C shows an exemplary apparatus positioned within a passageway in accordance with one embodiment of the invention. Specifically, FIG. 11A shows an image of the detectable markers on the apparatus which indicates that the apparatus is correctly positioned in accordance with on embodiment of the invention. Conversely, FIGS. 11B and 11C each show an image of the detectable markers on the apparatus which indicate the apparatus is incorrectly aligned in accordance with various embodiments of the invention;

FIG. 12 shows the partial blockage of a passageway by a stent which may be undetectable using prior art methods;

DETAILED DESCRIPTION OF THE INVENTION

Portions of the description below will discuss various medical conditions and how novel methods using catheters and stents may be used to aid in the treatment these medical conditions. Certain methods implement novel catheters and/or stents. It is noted that the methods and apparatus disclosed are not limited to the treatment of the medical conditions disclosed but may be used to treat other medical conditions where appropriate. Thus, in one embodiment, the passageway may be a blood vessel. In one embodiment, the passageway comprises an aorta. In one embodiment, the passageway may a coronary artery. In other embodiments, the passageway may include a portion of two or more coronary arteries.

Figure 2:
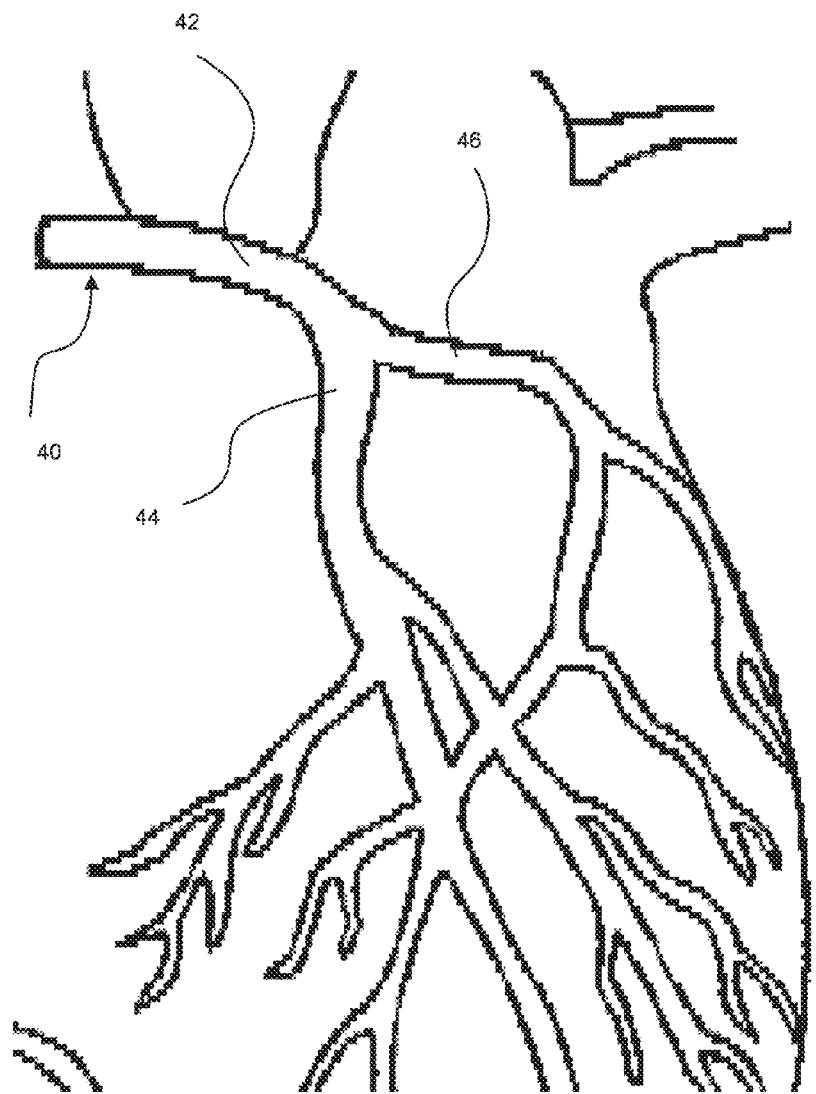
FIG. 2 illustrates an enlarged view of the human heart in FIG. 1, illustrating the left main coronary artery.

In other embodiments, the passageway includes several blood vessels. For example, the passageway may comprise one or more junctions, such as shown in FIG. 2 below. Those skilled in the art will readily appreciate that any blood vessel (inclusive of any junctions on those vessels), such as arteries, veins, and/or capillaries, are within the scope of passageway as used herein.

Further, while the passageways shown in the exemplary embodiments described below refer to blood vessels, these are merely exemplary. Any passageway in a living being that may transport liquids and/or gases, either alone, in combination with each other and/or with one or more solids are within the scope of this disclosure. Indeed, any passageway within a living being within the scope of this disclosure, inclusive but not limited to: sinuses, orifices, cavities, and renal vessels.

Figure 1:
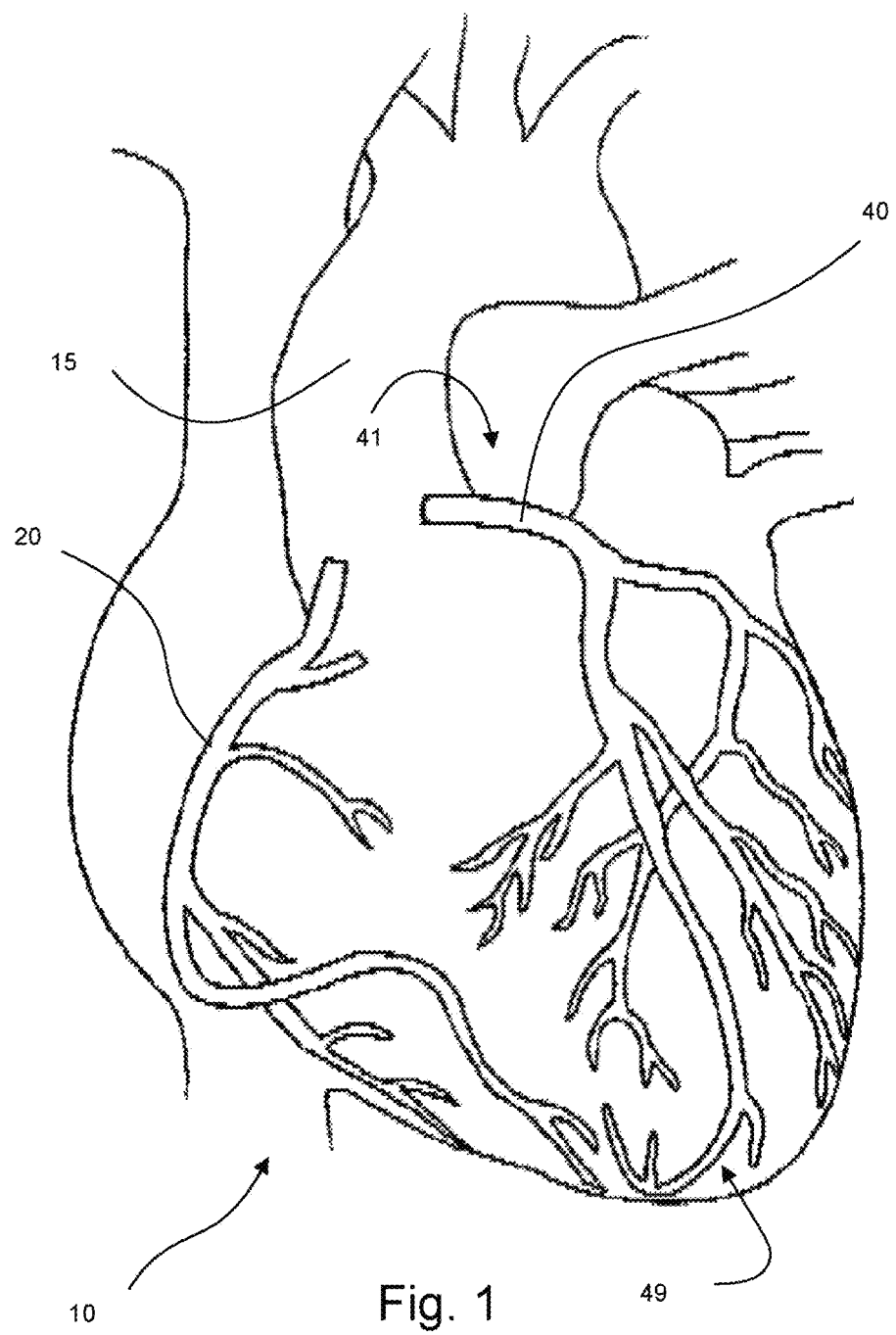
FIG. 1 illustrates an embodiment of a human heart.

Looking first at FIG. 1, an embodiment of a heart 10 is depicted. The heart 10 is fed by a right coronary artery 20 that branches out and provides blood to a portion of the heart. A left coronary artery 40 is also shown and also branches out and provides blood to a portion of the heart. As can be appreciated, a blockage at the beginning or proximal end 41 of the left coronary artery 40 would affect the flow of blood to all points downstream while a blockage at the distal end 49 of the left coronary artery 40 might have little or no discernable effect on the viability of the heart 10.

Turning to FIG. 2, the left coronary artery 40 is shown in an enlarged view that includes the left main artery or main branch 42 that feeds a first branch 44 (which as depicted is the left anterior descending artery) and a second branch 46 (which as depicted is the left circumflex artery).

Figure 3:
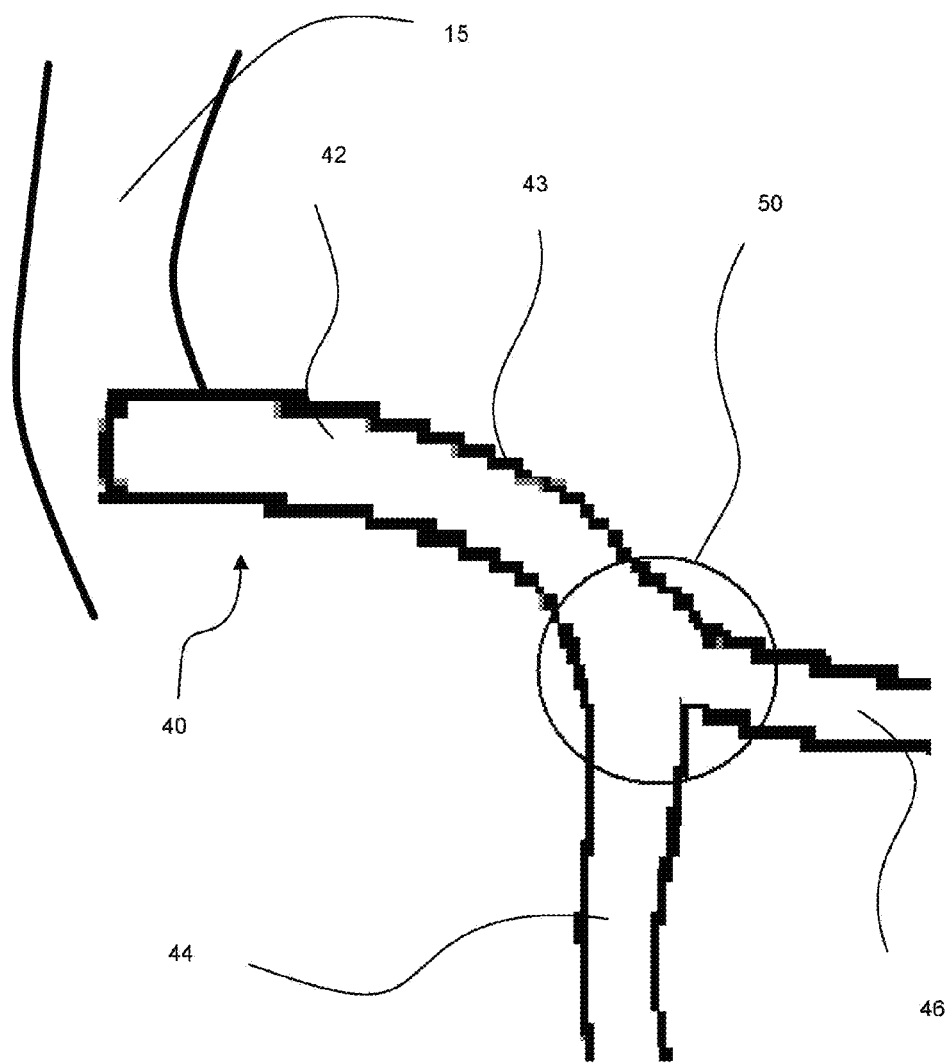
FIG. 3 illustrates a further enlarged view of the left main coronary artery of the human heart depicted in FIG. 2.

As depicted in FIG. 3, the first branch 44 shows a further enlarged view of the left coronary artery 40. The main branch 42 forms a junction 50 where it bifurcates into the first branch 44 and the second branch 46. As can be further appreciated, the main branch 42 includes a wall 43. In order for blood to flow through the left coronary artery 40, the wall 43 forms a tube-like shape that preferably is free from blockage.

Figure 4:
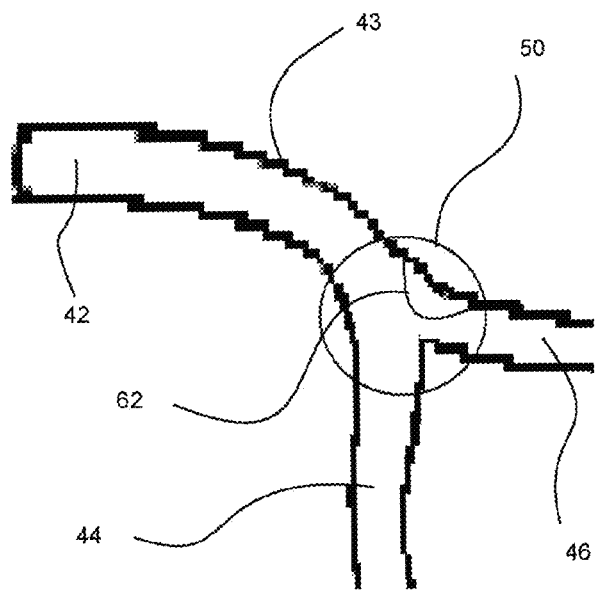
FIG. 4 illustrates an embodiment of blockage in an artery of a human heart in accordance with an aspect of the present invention.
Figure 5:
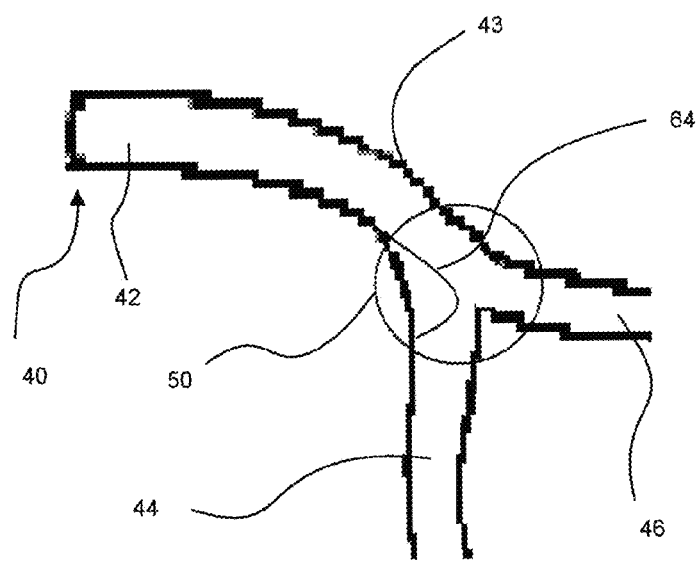
FIG. 5 illustrates an alternative embodiment of blockage in an artery of a human heart in accordance with an aspect of the present invention.

Unfortunately, as shown in FIG. 4, a blockage 62 may be formed by, for example, deposits of fatty tissue on the wall 43 in the junction 50. In FIG. 4, the blockage 62 partially occludes the flow of blood into the second branch 46. FIG. 5 depicts a similar situation except that the blockage 64 partially occludes the first branch 44.

Figure 6A:
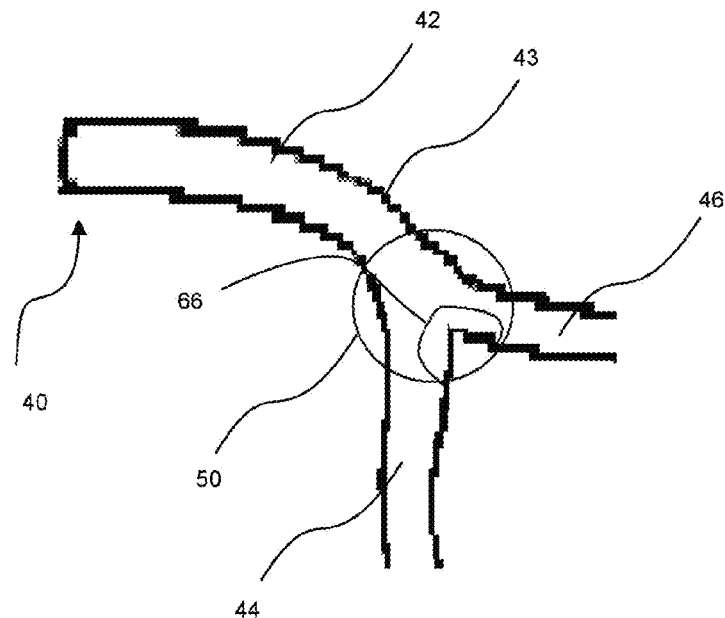
FIG. 6a illustrates an alternative embodiment of blockage in an artery of a human heart in accordance with an aspect of the present invention.
Figure 6B:
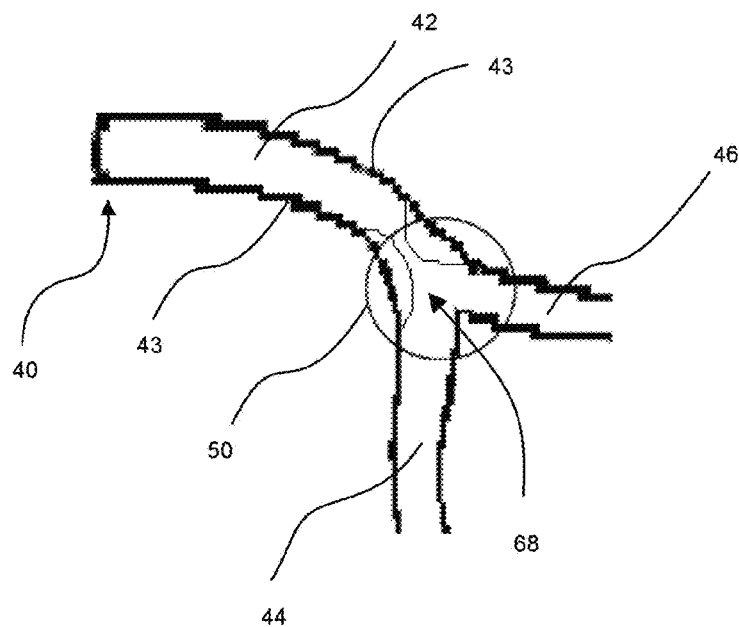
FIG. 6b illustrates an alternative embodiment of blockage in an artery of a human heart in accordance with an aspect of the present invention.

FIG. 6a illustrates a blockage 66 in the junction 50 that occludes blood flow to both the branch 44 and the branch 46. FIG. 6b illustrates a blockage 68 that is not within the junction 50 but affects blood flow to the first branch 44 and the second branch 46. As can be appreciated by FIG. 4-6b, blockage in or near the junction 50 tends to require a solution that allows blood to flow to both branches 44, 46. It is noted that numerous other configurations of blockage near or in the junction 50 are possible. In an embodiment the blockage will occlude the main branch; in alternative embodiments the first branch or the second branch or a combination of two or more branches will be occluded by the blockage.

Figure 7:
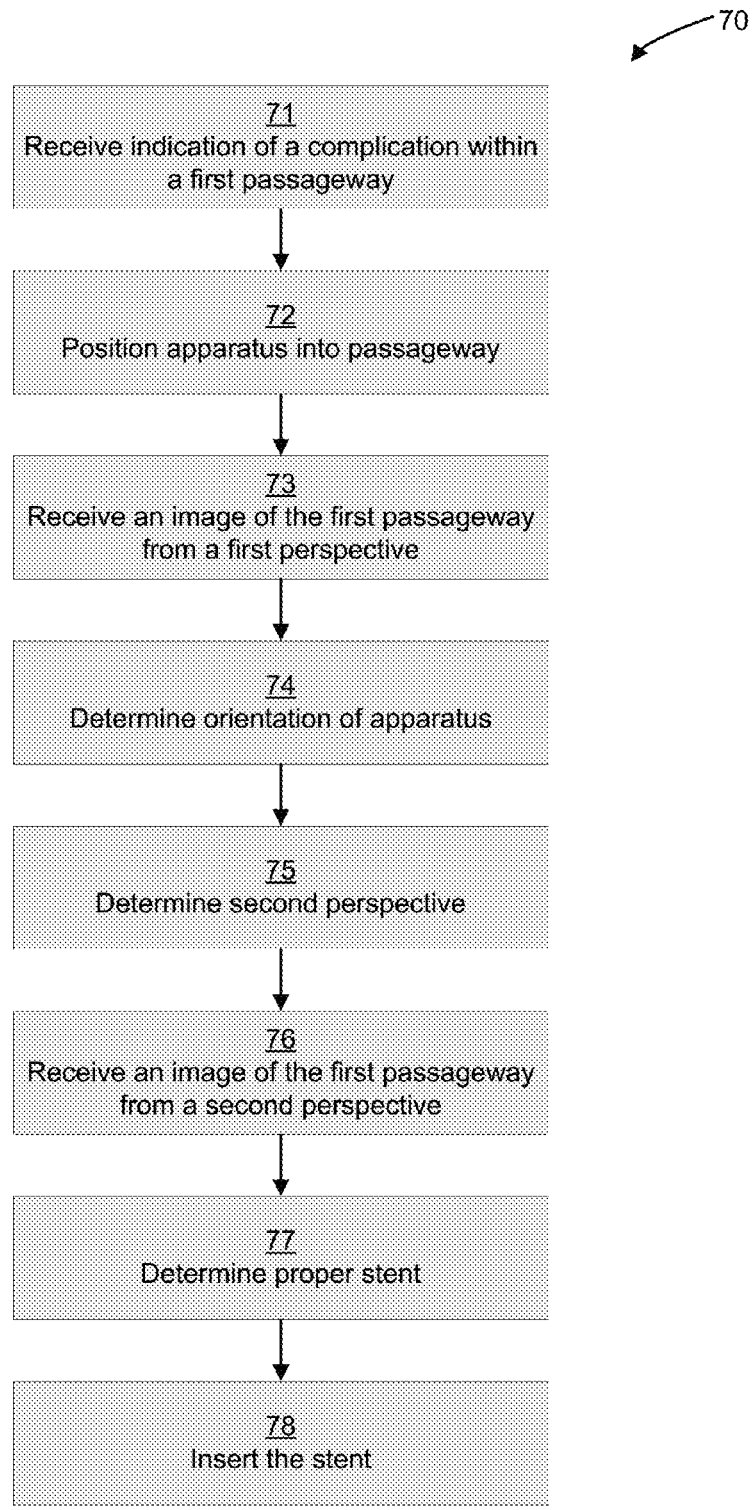
FIG. 7 is a flowchart of one exemplary method in accordance with one embodiment of the invention.

FIG. 7 is a flowchart 70 of an exemplary process in accordance with one embodiment of the invention. Those skilled in the art with the benefit of this disclosure will readily appreciate that additional or fewer blocks may be implemented within flowchart 70 without departing from the scope of this disclosure. Moreover, the ordering of the blocks within flowchart 70 are provided for conveying one of many embodiments. In this regard, unless otherwise stated, the performance of one or more processes may be performed in any order and/or occur simultaneously.

In the exemplary embodiment shown in flowchart 70, block 71 may be implemented to receive an indication of a complication, such as a blockage or aneurysm, within a passageway. In one embodiment, the indication may comprise an angiogram or any other image depicting or representing the passageway. As used herein, the term "image" is inclusive of any media or output, such as for example, photographic, photolithic, and/or radio, magnetic, electric, or electro-magnetic fields that shows one or more properties of the imaged passageway. In this regard, an "image" as described herein may include electronic data that comprises information regarding a representation of the passageway. For example, electronic data may include "pixel data."

There is no requirement that the "image" be displayed as captured, but rather may be presented numerically as certain distances measured within an image. For example, in one embodiment a quantitative analysis may be performed on electronic data to provide an output that provides the results of the quantitative analysis. In one embodiment, the capturing of an image may include the use of labeled compositions that may be picked up by certain imaging equipment (such as graphically represented on a display or x-ray film). In one embodiment, the image may comprise an angiogram, or data derived from an angiogram.

Figure 8:
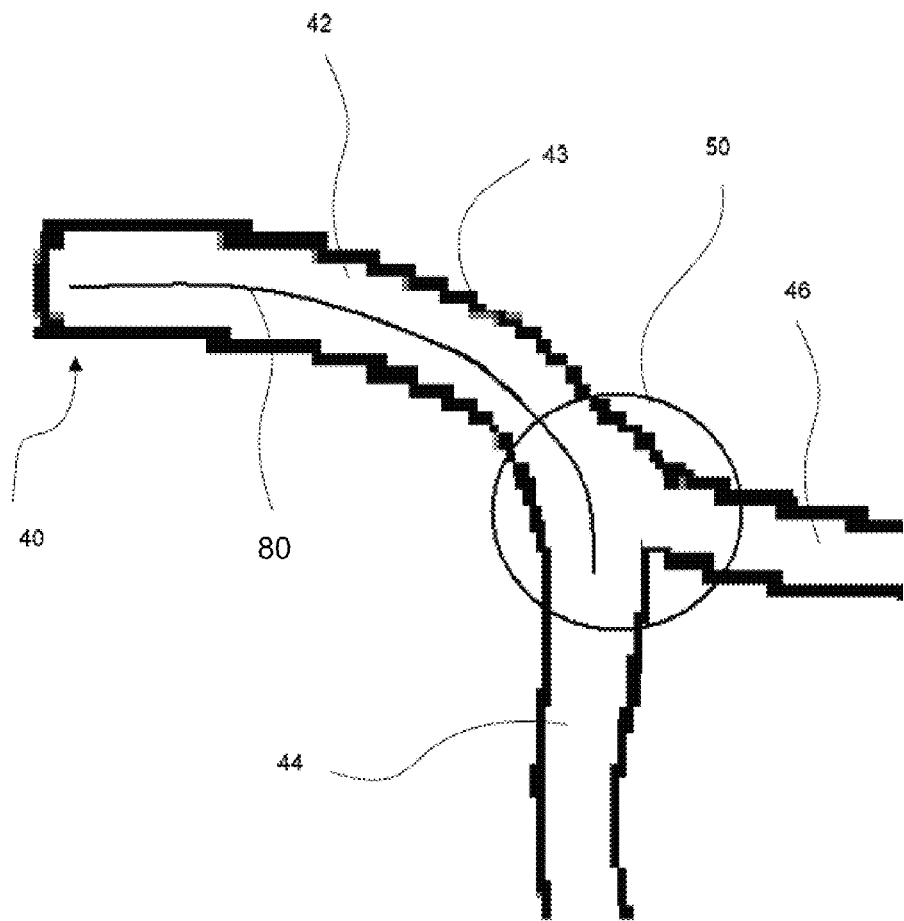
FIG. 8 illustrates an exemplary insertion of a guide wire into a coronary artery in accordance with one embodiment of the present invention.

An image capturing device (such as an x-ray device) may be used as part of block 71 to capture an image. For example, turning briefly to FIG. 8, an illustration of a passageway (left coronary artery 40) is provided. Blockage of the coronary artery 40 is omitted for the sake of clarity. In an embodiment, a guide wire 80 may be inserted into the left coronary artery 40 in a known manner. In one embodiment, the guide wire 80 may be associated with a catheter or other device to dispense an imaging substance into the passageway (i.e., the left coronary artery). For example, a catheter may be passed over and guided by the guide wire 80. The catheter or other device may be used to inject one or more radiopaque contrast materials into the passageway (i.e., left coronary artery 40). In one embodiment, a pigtail catheter may be used. As depicted in FIG. 8, the guide wire 80 may be inserted into the junction 50 and extends into the first branch 44. As can be appreciated, the distance the guide wire 80 extends into the junction 50 may be adjusted depending on the location of the blockage.

Figure 9:
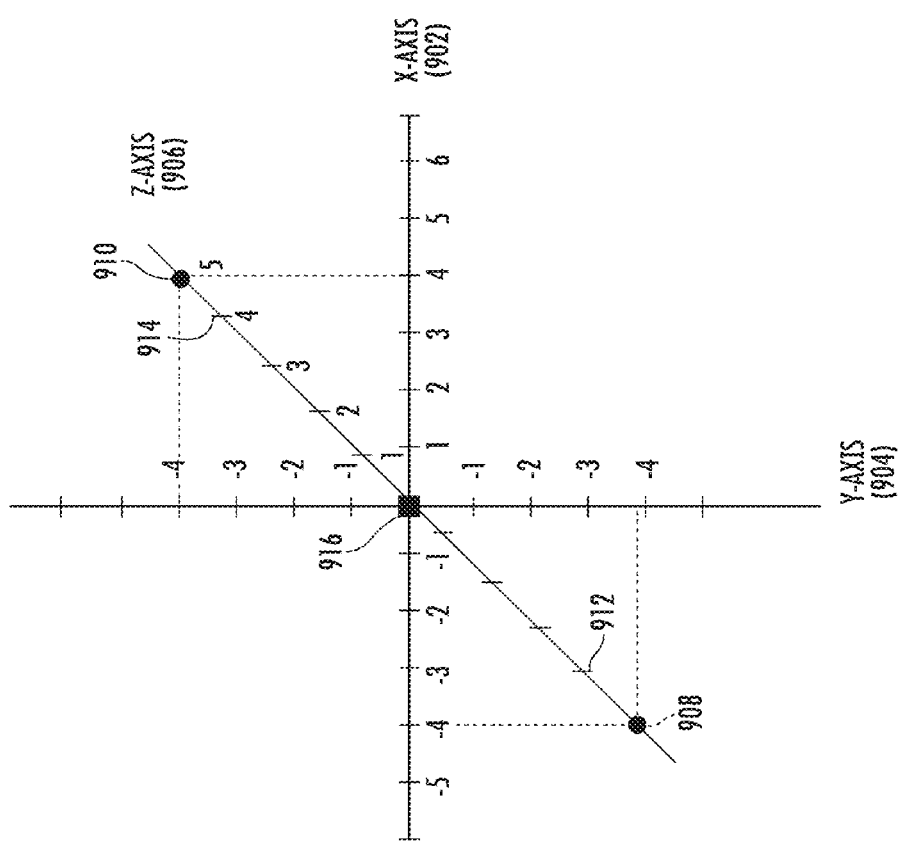
FIG. 9 shows a graphical representation of three main geometric axes.

An image obtained from block 71 may be used to determine where an occlusion or other complication is located. For example, in one embodiment the image is from a first perspective. As used herein, one perspective would be different from a second or additional perspective if the orientation of the output is different. As known to those skilled in the art, any location (including a body's passageways) comprises three main axes which are often referred to as the x-axis, y-axis, and the z-axis. Looking to FIG. 9, for example, x-axis 902 may refer to a length, y-axis 904 refer may refer to a height, and the z-axis 906 may refer to the depth. Thus, because exemplary axis 906 measures depth, location 908 (having coordinates x-4, y-4, and z-5) would be coming out from the plane of the FIG. and towards the viewer, whereas location 910 (having coordinates x4, y4, z5), would be extending away from the viewer. Because of this, the distance between 908 and 912 may appear to be larger than the distance 910 and 914 on an image despite the fact that each represent the same distance. The implications of this will be discussed in more detail below.

Returning to the discussion of perspective, capturing an image of an object located at point 916 (x0, y0, z0) from any of the points 908, 910, 912 and 914 would be from a different perspective because at least two of the coordinates along the x, y, or z axis would differ. For example, if only one of the x, y, or z axes differs, the perspective would be the same and only the "zoom" ratio would be altered Reception of an image (inclusive of any image data or data derived from the capture) may allow a medical professional to determine the location of the complication as well as better determine a remedy. For example, based upon the image, a specific type or sized tool, catheter, and/or stent may be chosen for diagnosing and/or treating the malady. However, without knowing the exact orientation of the passageway at the point of complication may result in inefficient and/or dangerous complications.

FIG. 10A shows an exemplary passageway comprising the three main axes. Looking to the exemplary passageway 1000 of FIG. 10A, an imaginary x-axis refers to the length, the y-axis refers to the height, and the z-axis refers to the depth of the passageway. For example, the length of the passageway 1000 may be measured along its longitudinal axis 1002. The height of the exemplary passageway 1000 by double-sided arrow 1004 and the depth is shown by double-sided arrow 1006. Because FIG. 10A shows a cross-section view of passageway 1000 along the longitudinal axis 1002, the portion of arrow 1004 that extends out of the cross-section displayed is shown as dashed.

For cylindrical passageways, the depth and width (1004/1006) are substantially equal and may be interchangeably referenced by the radius of the passageway. As also readily understood by those skilled in the art and reflected in the attached FIGS., most passageways located in a living being will rarely, if ever, travel a straight line. In fact, most passageways twist, turn, bend, flex, and/or traverse several different directions along the length. Therefore, the length of at least a portion of a passageway (or device within the passageway) may be used to refer to the x-axis, although it may not be substantially parallel with longitudinal axis 1002 shown in FIG. 10A. Those skilled in the art further appreciate that minor axes exist at almost an infinite number of locations and may extend away from the x-axis, and/or simultaneously traverse the y-axis and the z-axis.

Figure 10B:
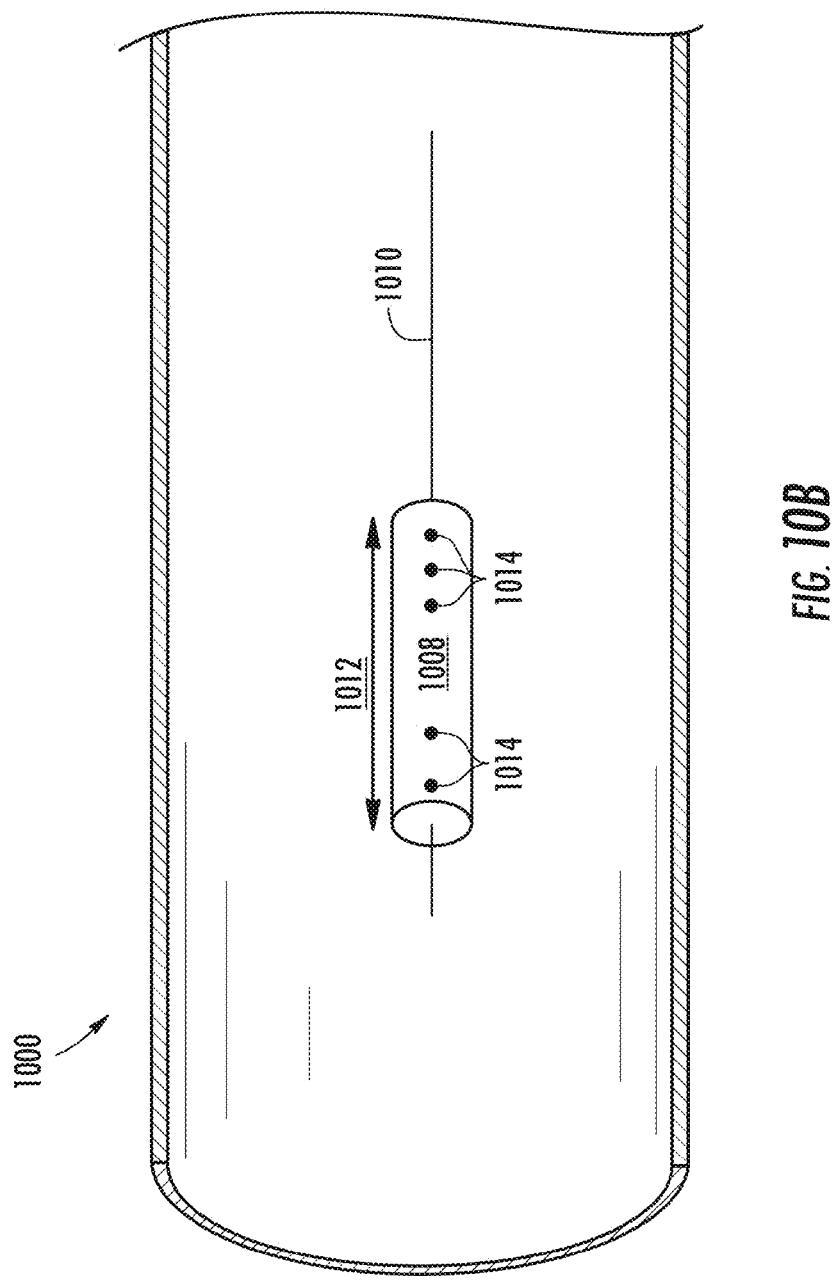

Aspects disclosed herein relate to systems and methods to determine orientation of a location along a passageway's length. In certain embodiments, a novel apparatus may be positioned into the passageway (block 72). FIG. 10B shows one exemplary apparatus 1008 being inserted into passageway 1000. Apparatus 1008 may be guided (for example, by guide wire 1010) through passageway 1000 while in a first compressed configuration and may later be expandable to a second configuration. While in the compressed configuration, the outer portion of apparatus 1008 may comprise a sheath or covering that assists maneuvering the apparatus 1008 through one or more passageways leading to (and including) passageway 1000. In certain embodiments, the outer surface of the apparatus 1008 may further comprise one or more biocompatible and/or anticoagulant materials. Apparatus 1000 may have a length (represented by double arrow 1012) that is substantially parallel to the longitudinal axis of the passageway 1000. In certain embodiments, information obtained from block 71 (and/or block 73, which is discussed below) may be considered when determining the location to position apparatus 1008 within the passageway 1000.

In certain embodiments, apparatus 1000 may comprise a plurality of markers, such as plurality of marks 1014. In one embodiment, the plurality of markers 1014 are positioned along the length (i.e., parallel to double arrow 1012) of the apparatus 1008. Depending on the embodiment, the plurality of markers 1014 may be separated by a predetermined distance. The distance may depend on the intended usage. For example, an apparatus 1008 intended to be used in an aorta may have markers that are separated by a larger distance than an apparatus 1008 that is intended for the renal artery. As used herein, the term "marker" includes any material or composition that is intended to be detectable by an imaging apparatus in a manner to be discernable from a non-marker portion of the apparatus, such as apparatus 1008.

Figure 10C:
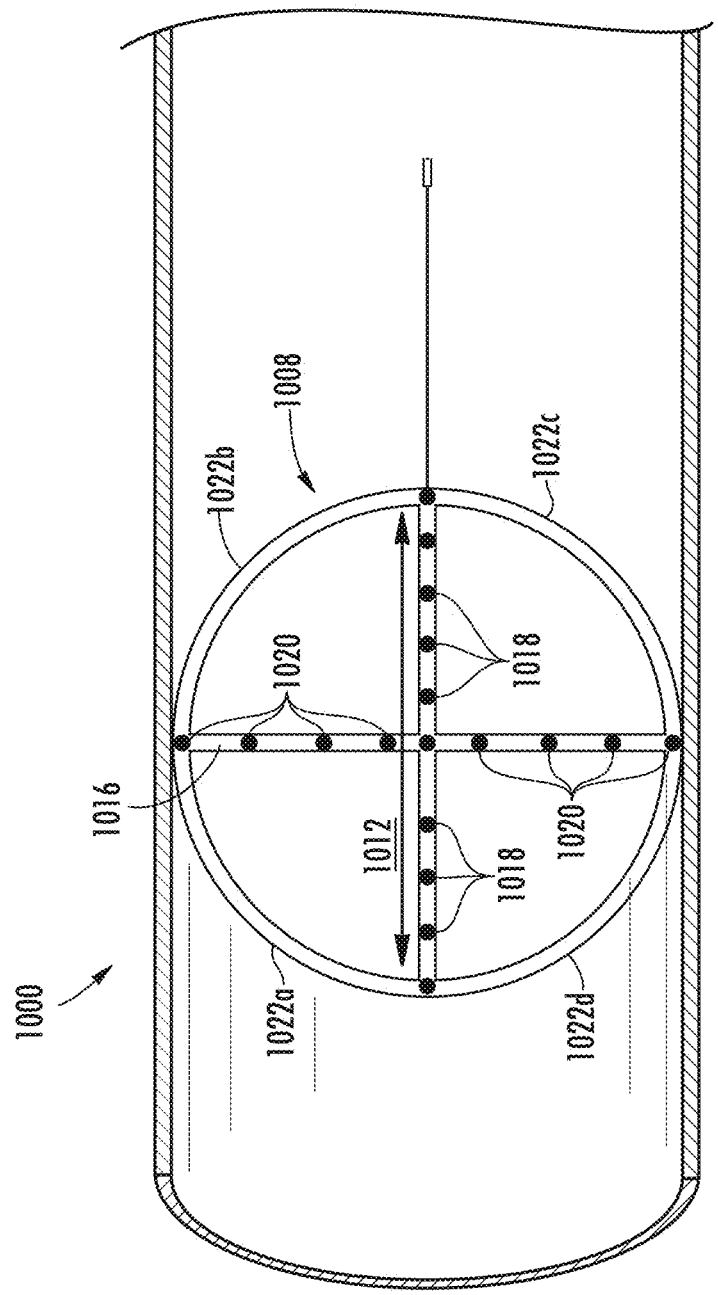

Upon being positioned at a desired location within passageway 1000, apparatus 1008 may be expanded to a second position or configuration. In one embodiment, apparatus 1008 is associated with a guide wire 1010, such that pulling an end of the guide wire 1010 (for example by a medical professional) causes the apparatus 1008 to expand to the second configuration. FIG. 10C shows exemplary apparatus 1008 expanded to the second position. As seen, at least a portion of apparatus 1008 expands away in two substantially opposing directions along a second axis. Specifically, in the illustrated embodiment, structure 1016 extends away from the longitudinal axis (see 1002 of FIG. 10A) in a substantially perpendicular manner. Thus, structure 1016 is substantially parallel with axis 1004 shown in FIG. 10A. In the illustrative embodiment, apparatus 1008 is within a cylindrical passageway, such that the direction of expansion should be relatively the same regardless of the direction because the diameter of the cylinder should be uniform. However, measuring along two or more opposing directions may further assist any determination whether the apparatus (or subsequent devices) or properly positioned. Regardless, in further embodiments, structure 1016 may be along any major or minor axis that transects the longitudinal axis (1002 of FIG. 10A).

The expansion of apparatus 1008 from the first configuration to the second configuration may depend on a myriad of factors. In one embodiment, apparatus may have a known predetermined expansion. The selection of such an apparatus may consider, among other factors, the type of passageway it will be expanded within and/or unique properties of the passageway within the specific living being. In certain embodiments, information obtained or derived from block 71 may be utilized when determining to use an apparatus with a predetermined expansion. In another embodiment, the apparatus may expand to the second configuration until resisted by a predetermined force. For example, apparatus 1008 may be configured to keep expanding (to a certain extent) until it contacts (and/or exerts a predetermined amount of force) the inner perimeter of the passageway 1000. This may be useful for ensuring proper placement, accurate measurements of the passageway (described below), and/or ensuring apparatus 1008 does not shift to a different location.

While the expansion of apparatus 1008 has been described in the context of expanding along a single axis, those skilled in the art will understand that apparatus 1008 may expand along multiple axis. As described above, the expansion of a cylinder will result in the expansion of the entire circumference of the cylinder. Furthermore, the length (shown as element 1012) in FIG. 10B of apparatus 1008 may increase upon expansion from the first position to the second position. This may be useful in certain embodiments, for example, where apparatus 1008 must pass through smaller passageways before being expanded.

As further seen in FIG. 10C, upon expansion to the second position, apparatus 1000 comprises a plurality of markers 1018 along at least a portion of the apparatus' length. In one embodiment, plurality of markers 1018 may comprise at least a portion plurality of markers 1014. Depending on the embodiment, the plurality of markers 1018 may be separated by a predetermined distance. The distance may depend on the intended usage, for example, as discussed above. Apparatus 1000 may further comprise a second plurality of markers 1020 along additional axes. For example, in the illustrated embodiment structure 1016 comprises plurality of markers 1020. The second plurality of markers 1020 may also be separated by a predefined distance. In one embodiment, the distance between two markers of the second plurality of markers 1020 may be different than the distance between two markers of the first plurality of markers 1018. In other embodiments, the first plurality of markers 1018 are positioned along the "width" of the passageway and the second plurality of markers 1020 are positioned along the "depth." This may be advantageous for non-cylindrical passageways, such as at a location of a turn or twisting passageway. Further, it may be advantageous at a junction.

Apparatus 1008 may further comprise one or more structures, such as structures 1022*a*-1022*d*) that may provide structural support for apparatus 1000 upon expanded into the second configuration. In certain embodiments, one or more of structures 1022*a*-1022*d* may assist in protecting the inner lining or surface of the passageway 1000 from any damage caused by apparatus 1000. While the exemplary structures 1022*a*-1022*d* are shown as being located proximate to the outer perimeter of apparatus 1000, one or more of the structures 1022*a*-1022*d* may be located further from the perimeter.

Whether or not structures 1022*a*-1022*d* provide structural support, other embodiments may use structures 1022*a*-1022*d* as markers (either singularly, in conjunction with each other, or together with other markers (such as markers 1018, and/or 1020)). In this regard, the plurality of markers 1018 along 1012 may travel along substantially the same dimensions as structure 1022*a*-1022*d*, however, appear to be along a straight line due to the perspective of FIG. 10C. Looking for example to FIG. 10D, the plurality of markers 1018 are shown to travel along axis 1006 in addition to axis 1002. Thus, when taken from the perspective shown in FIG. 10D, the portion of markers on the forefront appear lower on the image than the portion of the markers that are behind axis 1002. Although FIG. 10D as well as the other FIGS. of this disclosure show a plurality of markers, those skilled in the art will appreciate that a single marker may be used to span across one or more axes.

In one embodiment, a second image of at least a portion of the passageway may be received (block 73). The use of "second" in reference to the image is merely to differentiate block 73 from any image captured and/or received at any other process. Those skilled in the art with the benefit of this disclosure will readily appreciate that the recited first image is not required to occur before the capture of the second image. In this regard, a first image as described above is not required in accordance with certain embodiments. The second image may be captured following the expansion of 1000 apparatus to the second position/configuration. The image may be configured to capture data regarding at least a portion of the markers within the first and/or second plurality of markers 1018, 1020. The image received at block 73 may have been captured with different imaging equipment than one or more images obtained at block 71.

Figure 10E:
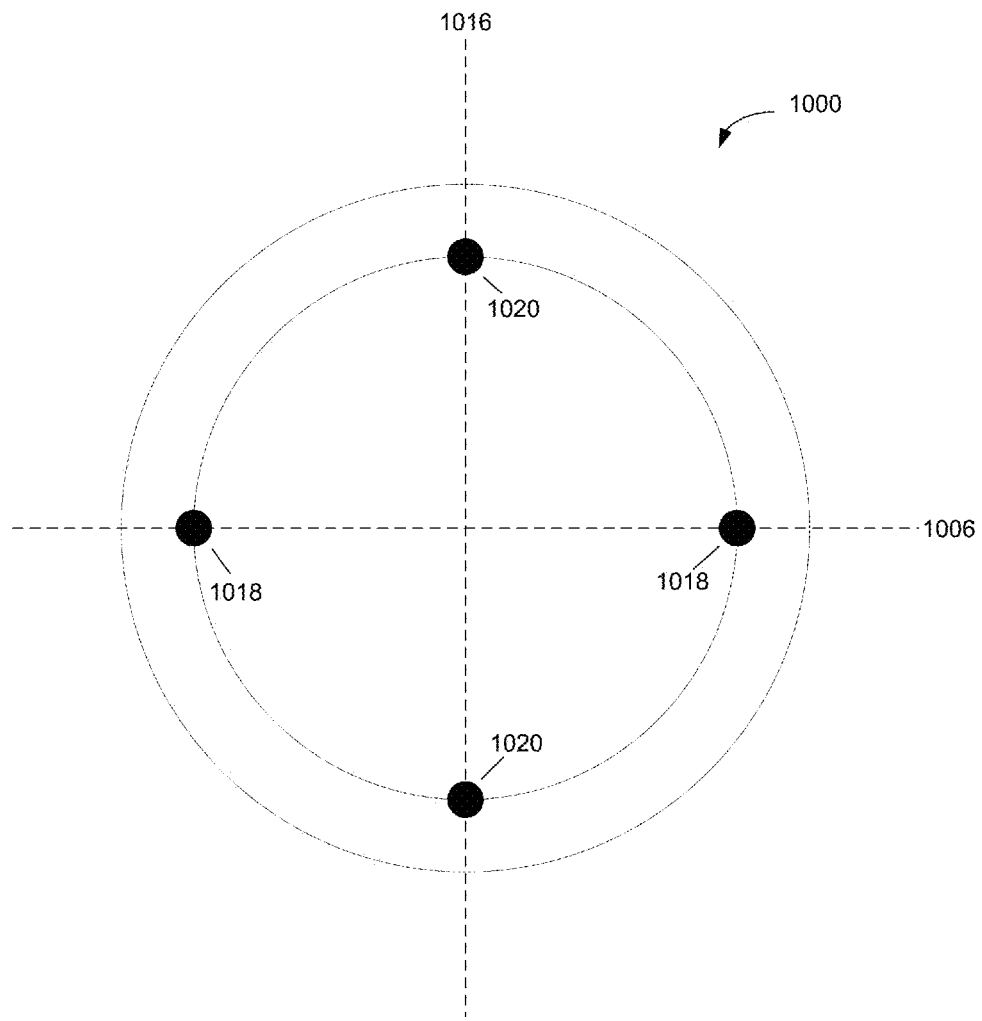

FIG. 10E shows a planar view of the passageway 1000 and exemplary apparatus 1008 of FIG. 10D along dotted line 1024 shown in FIG. 10D. (which is substantially aligned and parallel with the longitudinal axis 1002). As seen, at least two markers from the plurality of markers 1018 may be located along axis 1006 at about two opposing locations of the inner diameter of passageway 1000. Likewise at least two markers from the plurality of markers 1020 may be located along axis 1016 (see, e.g. FIG. 10C). As shown, the two markers from the plurality markers 1020 may be located at about two opposing locations of the inner diameter of passageway 1000. In this regard, the inner diameter of passageway 1000 may be detected along two axes.

In one embodiment, block 74 may be implemented to assist determining the orientation of apparatus 1008 within a passageway. FIGS. 11A-11C show exemplary images that capture or otherwise represent plurality of markers 1018 of apparatus 1008. As shown in FIGS. 11A-11C, the plurality of markers 1018 comprise markers 1018*a*-1018*d*. Those skilled in the art will appreciate that the shape, quantity, and/or configuration of markers 1018*a*-1018*d* may be different among various embodiments. Furthermore, there is no requirement that an image pick up every marker within plurality of markers 1018. Further, in certain embodiments, a first plurality of markers, such as plurality of markers 1018 may be configured to be detectable by one imaging technique, while a second plurality of markers (such as plurality of markers 1020 shown in FIG. 10C) may be configured to be detectable using a second imaging technique. This may be advantageous, for example, if several markers are used on multiple axes.

Looking first to FIG. 11A, markers 1018a-1018d are positioned at about the longitudinal axis passageway 1000. The remaining portion of apparatus 1008 is omitted for clarity; however, those skilled in the art will understand that, depending on the imaging technique, at least a portion of the apparatus 1008 may be captured on the image. Of importance in the fact that the markers 1018a-1018d shown in FIG. 11A appear to be relatively the same size and distance apart from each other. Thus, such an image would indicate that the length of apparatus 1008 is substantially parallel with the longitudinal axis of passageway 1008.

Looking to FIG. 11B, however, shows an image where apparatus 1008 is not parallel with the longitudinal axis of passageway 1000. Rather, the portion of the apparatus 1008 proximate to marker 1018a is towards the image capturing device, while the portion of the apparatus 1000 proximate 1018d appears to be further from the image capturing device. This misalignment of apparatus 1000 may be observed from one or more observations on an image, such as represented in FIG. 11B. First, in certain images, such as that represented in FIG. 11B, markers closer to the image capture device will appear brighter or larger in an image. For example, marker 1018a appears larger than the other markers, with each successive marker travelling from marker 1018a-1018d appearing smaller or "less bright" than the preceding marker, thus marker 1018d appears to be the smallest. A second observation that may be noticed in the image represented by FIG. 11B, either alone or concurrently with the first observation, is that the distance between the markers 1018a-1018d appears to decrease along the distance from marker 1018a to marker 1018d.

Likewise, the image represented by FIG. 11C shows misalignment of the apparatus (element 1008, shown in FIGS. 10A-10C) in the opposite direction. Specifically, the portion of the apparatus 1000 proximate to marker 1018a is further from the imaging device than the portion of the apparatus proximate to marker 1018d. For example, marker 1018a is smaller or appears "less bright" than marker 1018d and the distance between markers appears to decrease as the distance from marker 1018a to marker 1018d is traveled. Thus, use of apparatus 1008 may be used to determine if insertion of a stent or other tool within passageway may be misaligned (see. e.g., block 74 of FIG. 7). Apparatus 1008 may prevent the misinterpretation of prior art imaging data that may indicate a stent or other object within a passageway is aligned, however, only appears to be aligned due to parallax. FIG. 12 more clearly illustrates the problem that may be caused by parallax.

FIG. 12 shows exemplary stent 1228 positioned within passageway 1200, which may be passageway 1000. In certain instances, it may be desirable to ensure stent 1228 or other medical devices are directly aligned at boundary 1226, such that the length of stent 1228 does not extend to the left of boundary 1226 (and thus potentially occlude a portion of passageway 1224). Using prior art methods and systems, it may be determined that the length of stent 1228 does not extend to the left of boundary 1226. Using methods and systems disclosed herein, such as the use of markers on one or more axis of apparatus 1000 shown in FIGS. 10A-10C and 11A-11C, it may be determined that a different perspective may be best suited for implanting stent 1228 and/or that stent 1228 should be implanted in a different orientation Using a second perspective, for example, as a result of obtaining the results shown in FIGS. 10A-10C may reveal that the true outline of stent 1228 is really shown with border 1230 (see, e.g., block 75 shown in FIG. 7). As seen, border 1230 is to the left of boundary 1226, thus at least a portion of the junction of passageway 1200 and 1224 may be blocked. Blockage of passageways is generally not desired and may lead to fatal consequences. Therefore, block 76 may be implemented, based upon the detected orientation of the apparatus, to obtain an image captured from a second perspective.

Figure 13:
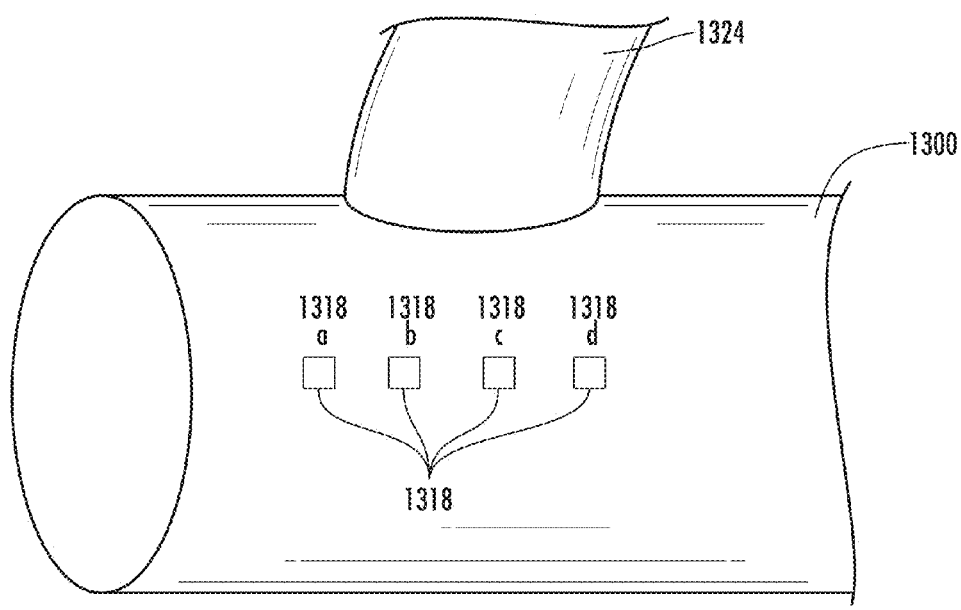
FIG. 13 shows an exemplary apparatus positioned at a junction of two passageways in accordance with one embodiment of the invention.

Further advantages of the disclosed methods and systems may include accurately determining properties of a second passageway that forms a junction with passageway. FIG. 13 is a cross-sectional perspective view of passageway 1300. As seen in FIG. 13, a plurality of markers 1318 provided along the longitudinal axis of passageway 1300. In one embodiment, the plurality of markers 1318 may comprise at least a portion of the plurality of markers 1018, shown in FIG. 10A-10C. Knowing the distance between the markers, for example, between 1318b and 1318c or even between 1318a and 1318d may assist any determination of the diameter of passageway 1324 at the junction with passageway 1300. As discussed above, apparent differences between the "brightness" or size of the markers may indicate that an apparatus or stent is not correctly positioned. Thus, in certain embodiments, the selection of a stent or other device for positioning within a passageway (1000, 1200, 1300) may be based upon the positions of at least a portion of markers 1318 of the apparatus (block 77 of FIG. 7). As discussed above, while the exemplary plurality of markers 1308 are positioned along the longitudinal axis of the exemplary passageways 1000, 1200, 1300, those skilled in the art will understand that the markers may be positioned along any major or minor axis, including several axes.

Figure 14:
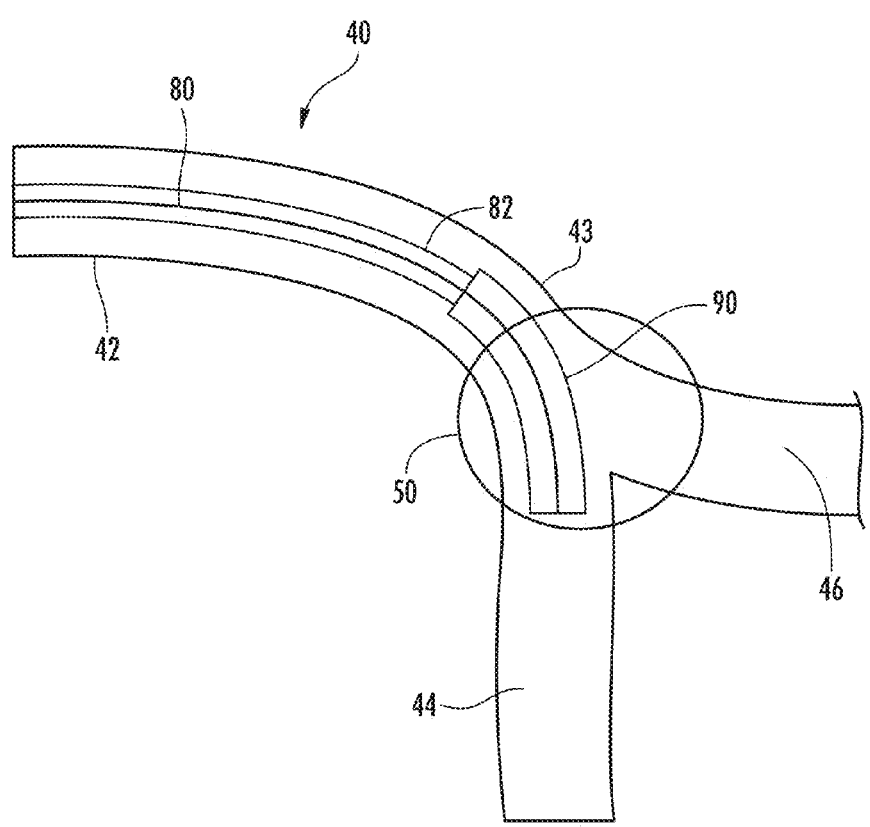
FIG. 14 shows the insertion of a stent in accordance with one embodiment of the invention.

Block 78 may be implemented to insert a stent (or medical device) in a passageway 1000, 1200, 1300 using the received data. FIG. 14, which is similar to and uses some of the same reference numerals as FIG. 8, shows the insertion of a catheter in accordance with one embodiment of the invention. After insertion of guide wire 80, a possible next block may be to guide a catheter 82 connected to an angioplasty balloon ("balloon") 90 along the guide wire 80 into the desired position. Once balloon 90 is correctly positioned, it may be inflated so as to open up the portion of the left coronary artery 40 that was stenosed by the blockage. To help keep the left main open, the balloon 90 includes the stent (not shown in FIG. 14) mounted on the exterior of the balloon 90. When the balloon 90 is expanded to open up the passageway, the stent is also expanded. Once the passageway is opened, the pressure inflating the balloon 90 is removed and the balloon 90 contracts. However, the stent remains in position so as to provide support for the wall 43 of the left coronary artery 40.

It should be noted that the balloon 90 may be compliant or non-compliant, depending on the intended use. Generally speaking, balloons that are non-complaint have a fixed amount of expansion and do not effectively increase in diameter in response to increases in internal pressure. In contrast, balloons that are compliant do effectively increase in diameter in response to increases in internal pressure. The balloon 90 may also be semi-compliant and thus provide some minimal amount of expansion in response to greater pressure. While different levels of compliance may be suitable for different situations, a non-compliant balloon may be useful to prevent the balloon 90 from expanding in the area where the side aperture is provided.

One concern regarding the use of angioplasty is restenosis. Restenosis, or the re-narrowing of the arteries, affects a percentage of patients receiving angioplasty. While the use of a stent in combination with the angioplasty has significantly reduced the occurrence, restenosis is still an issue. To address this potential problem it may be desirable to coat the stent with a pharmaceutical agent. While different pharmaceutical agents work differently, in an embodiment, the drug coating may be configured to provide an anti-restenotic or anti-neointimal proliferation effect. In an embodiment, the coating may be RAPAMYCIN or SIROLIMUS.

Stent 1228 may be one of many types of stents. In one embodiment, a stent disclosed in U.S. Pat. No. 7,632,304, issued Dec. 15, 2009 and/or U.S. patent application Ser. No. 12/614,228, filed Nov. 6, 2009, the contents of which are incorporated herein by reference in their entirety for any and all purposes. In an embodiment, the stent may be made of a stainless steel alloy, although other materials may be used. It is noted that the type of stent is not crucial; thus, for example but without limitation, a coiled spring design, a slotted tube design or mesh design may be used. However, one potential issue with the insertion of stents is that under certain known viewing methodologies the stent will not be visible (e.g. the stent will be radiolucent).

The present invention has been described in terms of preferred and exemplary embodiments thereof. Numerous other embodiments, modifications and variations within the scope and spirit of the appended claims will occur to persons of ordinary skill in the art from a review of this disclosure.

I claim:

1. An apparatus configured to be positioned within a passageway of a living being, the apparatus comprising:
 a structure configured to be selectively expanded from a first configuration to a second configuration, comprising:
  a first-stage outer wall having a length along a first axis, a depth along a second axis and a height along a third axis; and
  an expandable strut member configured to be selectively expanded along the second axis to a maximum expansion distance that is greater than the depth of the living passageway;
  wherein at the first configuration of the apparatus, the depth and a height of the first-stage outer wall form an outer perimeter of the apparatus that is less than an inner perimeter of the passageway of the living being, such that the length of the first-stage outer wall is configured to be maneuverable along a longitudinal axis of the passageway from a first location to a second location;
  wherein at the second configuration of the apparatus, the expandable strut member expands along the second axis until it reaches an interior surface of the passageway or a physical structure to form two opposing outer surfaces separated by a first inner diameter, wherein the first inner diameter is a distance that is less than the maximum expansion distance and further comprises a first plurality of markers that are each separated by a predetermined distance along the first inner diameter of the apparatus; and
  wherein the first plurality of markers are configured to be detected by an imaging device to allow an indication of an orientation of the apparatus and a diameter of the passageway.

2. The apparatus of claim 1, wherein the expandable strut member is a first expandable strut member, and the apparatus further comprises a second expandable strut member configured to be selectively expanded along the third axis to a maximum expansion distance that is greater than the depth of the living passageway, wherein at the second configuration of the apparatus, the first and the second expandable strut members each expand a distance that is less than their maximum expansion distance, and wherein the second expandable strut member comprises a second plurality of markers.

3. The apparatus of claim 2, wherein the maximum expansion distance of the first expandable strut member is not equal to the maximum expansion distance of the second expandable strut member.

4. The apparatus of claim 1, wherein the expandable strut member expands along a first direction and a second opposing direction.

5. The apparatus of claim 2, wherein the first plurality and the second plurality of markers are configured to be detected by an imaging device to allow an indication of an orientation of the apparatus and a diameter of the passageway.

6. The apparatus of claim 5, wherein at the second configuration, at least one marker is located at about each of the second axis outer surface and the third axis outer surface.

7. The apparatus of claim 1, wherein the apparatus is configured such that the length of the apparatus increases along the first axis upon expansion from the first configuration to the second configuration.

8. The apparatus of claim 7 wherein at least two markers are located on the structure along the first axis.

9. The apparatus of claim 2, wherein the position of at least a portion of the first or the second plurality of markers is configured such that when detected by imaging equipment allows the determination of an orientation of a catheter operatively connected to the apparatus.

10. The apparatus of claim 2, wherein the first plurality of markers are configured to be detected by a first imaging technique and the second plurality of markers are configured to be detected by a second imaging technique.

11. An apparatus configured to be expanded from a first configuration to a second configuration within a passageway of a living being, comprising:
 an outer wall extending along a first axis configured to be maneuvered within a passageway of a living being when the apparatus is at the first configuration such that the first axis is orientated along the longitudinal axis of the passageway;
 at least one expansion member configured to be selectively expanded along a second axis and a third axis, wherein the third axis is perpendicular to the second axis, wherein the at least one expandable strut member is configured to be expanded to a maximum expansion distance along the second axis that is greater than the depth of the living passageway and a maximum expansion distance along the third axis that is greater than the width of the living passageway;
 wherein upon being selectively transitioned from the first configuration to the second configuration, the at least one expandable strut member expands along the second axis and the third axis until reaching an interior surface of the passageway or a physical structure to form two opposing outer surfaces along each of the second axis and the second axis, the respective ends of the axes being separated by a first inner diameter and a second inner diameter that are each less than the maximum expansion distance and further comprise a plurality of markers that are each separated by a predetermined distance along the inner diameters of the first second and third axes; and a plurality of markers that are separated by a predetermined distance along each of the first and the second inner diameters of the apparatus, and configured to be detected by an imaging device to allow an indication of an orientation of the apparatus and a diameter of the passageway.

12. The apparatus of claim 11, wherein the outer wall is configured to be positioned over a catheter while in the first configuration.

13. The apparatus of claim 11, wherein the plurality of markers comprises a first portion and a second portion, wherein the first portion are configured to be detected by a first imaging technique and the second portion are configured to be detected by a second imaging technique.

14. The apparatus of claim 11, wherein at least a portion of an outer surfaces of the apparatus is spherical when the apparatus is at the second configuration.

15. The apparatus of claim 11, wherein at least one marker is located at about each of the second axis outer surface and the third axis outer surface when the apparatus is at the second configuration.

16. The apparatus of claim 11, wherein the apparatus is configured such that the length of the apparatus increases along the first axis upon expansion from the first configuration to the second configuration.

17. The apparatus of claim 11, wherein at least two markers are located on the structure along the first axis.

* * * * *